(12) United States Patent
Hong et al.

(10) Patent No.: US 8,858,780 B2
(45) Date of Patent: Oct. 14, 2014

(54) BIOSENSOR AND METHOD FOR DETERMINING AN ANALYTE CONCENTRATION

(75) Inventors: Chien-Chong Hong, Zhubei (TW); Meng-Hua Chung, Taoyuan (TW); Chih-Chung Lin, Taoyuan County (TW)

(73) Assignee: National Tsing Hua University, Hsinchu (TW)

( * ) Notice: Subject to any disclaimer, the term of this patent is extended or adjusted under 35 U.S.C. 154(b) by 473 days.

(21) Appl. No.: 13/301,105

(22) Filed: Nov. 21, 2011

(65) Prior Publication Data

US 2012/0234699 A1    Sep. 20, 2012

(30) Foreign Application Priority Data

Mar. 15, 2011   (TW) .............................. 100108745 A

(51) Int. Cl.
*G01N 27/327*   (2006.01)
*G01N 33/543*   (2006.01)

(52) U.S. Cl.
CPC .................................. *G01N 33/5438* (2013.01)
USPC ............................ 205/787; 205/792; 205/775

(58) Field of Classification Search
CPC . G01N 27/22; G01N 27/227; G01N 2600/00; G01N 27/3272; C12Q 2563/116
See application file for complete search history.

(56) References Cited

U.S. PATENT DOCUMENTS

| | | | | |
|---|---|---|---|---|
| 7,063,781 | B2* | 6/2006 | Murray et al. | 205/789 |
| 8,313,633 | B2* | 11/2012 | Li et al. | 205/183 |
| 2004/0126814 | A1* | 7/2004 | Singh et al. | 435/7.1 |

FOREIGN PATENT DOCUMENTS

JP            2006-28467 A  *  2/2006 ................ C08F 2/44

OTHER PUBLICATIONS

JPO computer-generated English language translation of Kitade et al. JP 2006-28467 A, patent published Feb. 2, 2006.*

* cited by examiner

*Primary Examiner* — Alex Noguerola
(74) *Attorney, Agent, or Firm* — Birch, Stewart, Kolasch & Birch, LLP

(57) ABSTRACT

A method of determining an analyte concentration employs a biosensor that includes a molecularly imprinted polymer film formed on a metal layer. The biosensor is connected to a charge/discharge circuit and charged and discharged during exposure to a solution containing an analyte. Voltage values during discharge are measured, and a characteristic parameter of the voltage values, which is associated with a concentration of the analyte detected by the biosensor, is determined. An unknown concentration of the analyte is determined by comparing the characteristic parameter to reference data representing a relation between known concentration of the analyte and the characteristic parameter of the biosensor. A biosensor, such as an anesthetic biosensor, is also disclosed.

17 Claims, 6 Drawing Sheets

BIOSENSOR AND METHOD FOR DETERMINING AN ANALYTE CONCENTRATION

CROSS-REFERENCE TO RELATED APPLICATION

This application claims priority of Taiwanese Patent Application No. 100108745 filed on Mar. 15, 2011.

BACKGROUND OF THE INVENTION

1. Field of the Invention

The invention relates to a biosensor and method for determining an analyte concentration, and more particularly to a method for determining a concentration of an analyte, such as anesthetic, using a molecularly imprinted biosensor.

2. Description of the Related Art

Based on different detecting mechanisms, conventional molecularly imprinted biosensors can be classified into different types of biosensors including optical biosensors and electrochemical biosensors. In the optical biosensors, a color reagent is required to be added into a solution to combine with an analyte in the solution for permitting optical detection of the concentration of the analyte. With a different detection mechanism, the electrochemical biosensors measure the electrochemical potential difference between electrodes to determine the concentration of the analyte without the need of using a color reagent.

Elodie Pardieu et al. "Molecularly imprinted conducting polymer based electrochemical sensor for detection of atrazine" Analytica Chimica Acta 649 (2009) 236-245, disclose an electrochemical electrode of a sensor capable of detecting the concentration of atrazine. The electrochemical electrode includes a platinum layer and a molecularly imprinted conductive polymer film formed on the platinum layer. In use, the electrochemical electrode and a reference electrode are placed into a solution containing the analyte, followed by performing cyclic voltammetric measurements so as to obtain a cyclic voltammogram for determining the concentration of the analyte. The conventional sensor is disadvantageous in that the material of the conductive polymer film is required to withstand the voltage, which is required to be sufficient to cause electrochemical oxidation-reduction in the solution, applied to the electrochemical electrode.

The entire disclosure of the aforementioned paper disclosed by Elodie Pardieu et al. is incorporated herein by reference.

The effect of anesthetic, such as propofol, to a patient depends on its brain concentration which is correlated to its blood concentration. Conventional detection of its blood concentration is normally conducted using liquid chromatography and GC-mass spectroscopy, which is complicated and time-consuming.

SUMMARY OF THE INVENTION

An object of the present invention is to provide a novel method of determining an analyte concentration using a biosensor that includes a molecularly imprinted polymer.

Another object of the present invention is to provide a novel method of determining an anesthetic concentration using a biosensor that includes a molecularly imprinted polymer.

According to one aspect of the invention, a method for determining a concentration of an anesthetic in a solution is provided. The method includes:

(a) providing a biosensor that includes two sensor electrodes each of which has a metal layer and a molecularly imprinted polymer film formed on the metal layer, said molecularly imprinted polymer film being imprinted by a template molecule to form a plurality of molecular recognition cavities for capturing molecules of the anesthetic;

(b) exposing the biosensor to the solution;

(c) connecting a charge/discharge circuit to the biosensor that has been exposed to the solution, the charge/discharge circuit including a discharge capacitor coupled between the sensor electrodes;

(d) applying a constant voltage to the charge/discharge circuit to charge the charge/discharge circuit and the biosensor;

(e) discharging the charge/discharge circuit and the biosensor after the charge/discharge circuit and the biosensor are charged saturatedly;

(f) measuring varying voltages across the discharge capacitor during discharge to obtain a set of varying voltage values that vary with time;

(g) determining a characteristic parameter of the voltage values associated with the concentration of the anesthetic detected by the biosensor; and (h) determining the concentration of the anesthetic by comparing the characteristic parameter with reference data representing a relation between an anesthetic concentration and characteristic parameters of the biosensor.

According to another aspect of the invention, a biosensor comprises a substrate and two sensor electrodes formed on the substrate. Each of the sensor electrodes including a metal layer and a molecularly imprinted polymer film formed on the metal layer. The molecularly imprinted polymer film is imprinted by a template molecule to form a plurality of molecular recognition cavities. The template molecule is anesthetic.

BRIEF DESCRIPTION OF THE DRAWINGS

In drawings which illustrate embodiments of the invention.

DETAILED DESCRIPTION OF THE PREFERRED EMBODIMENTS

Figure 1:
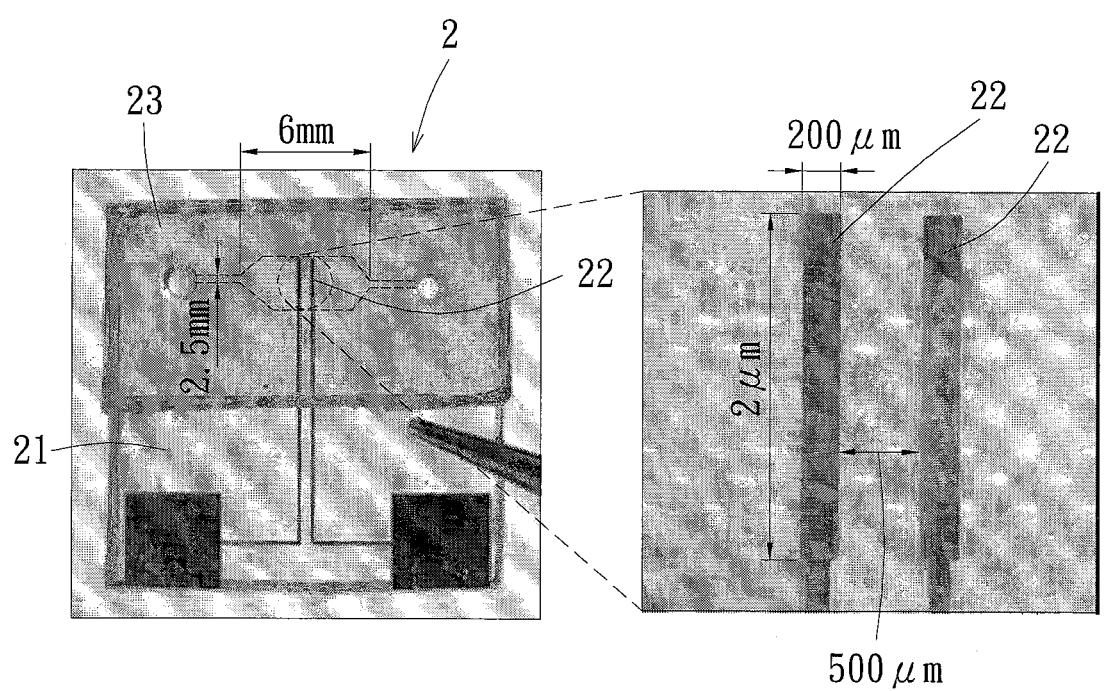
FIG. 1 is a plan view illustrating a preferred embodiment of a biosensor used in a method according to this invention.
Figure 2:
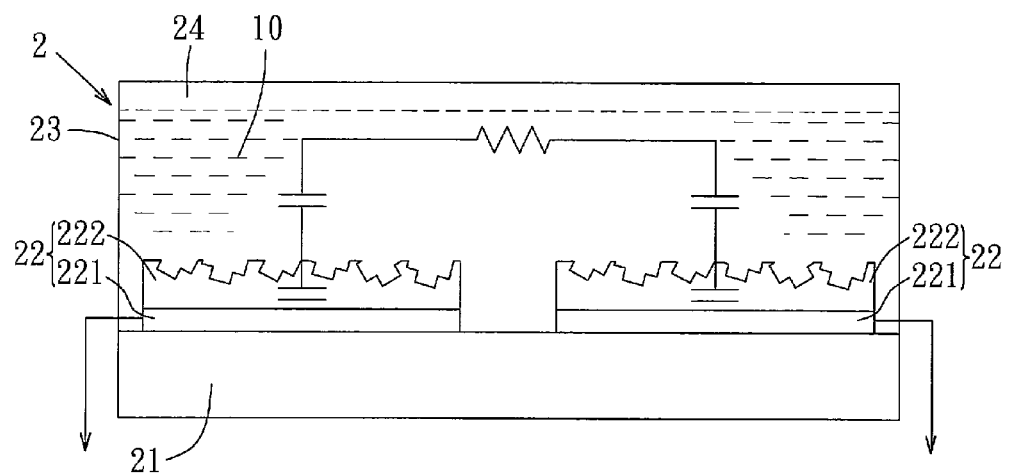
FIG. 2 is a schematic view illustrating sensor electrodes of the biosensor.

Referring to FIGS. 1 and 2, a biosensor 2 that can be used in a method of determining an analyte concentration according to the present invention. The biosensor 2 includes a substrate 21, two sensor electrodes 22, and an enclosure wall 23. Each of the sensor electrodes 22 includes a metal layer 221 formed on the substrate 21 and a molecularly imprinted conductive polymer film 222 formed on the metal layer 221. The enclosure wall 23 is sealingly bonded to the substrate 21 to define an inner space 24.

The biosensor 2 may be an anesthetic biosensor. The molecularly imprinted conductive polymer film 222 may be made from a conductive polymer. The conductive polymer is preferably formed from a monomer selected from pyrrole, acetylene, paraphenylene sulfide, thiophene, aniline, and isothionaphthene, and is more preferably pyrrole.

The molecularly imprinted conductive polymer film 222 is imprinted by a template molecule (the imprinting of a template molecule will be described in more details in the following examples) to form a plurality of molecular recognition cavities 223. The template molecule is preferably anesthetic, and is more preferably propofol. The metal layer 221 is preferably made from a noble metal, more preferably made from gold.

Figure 3A:
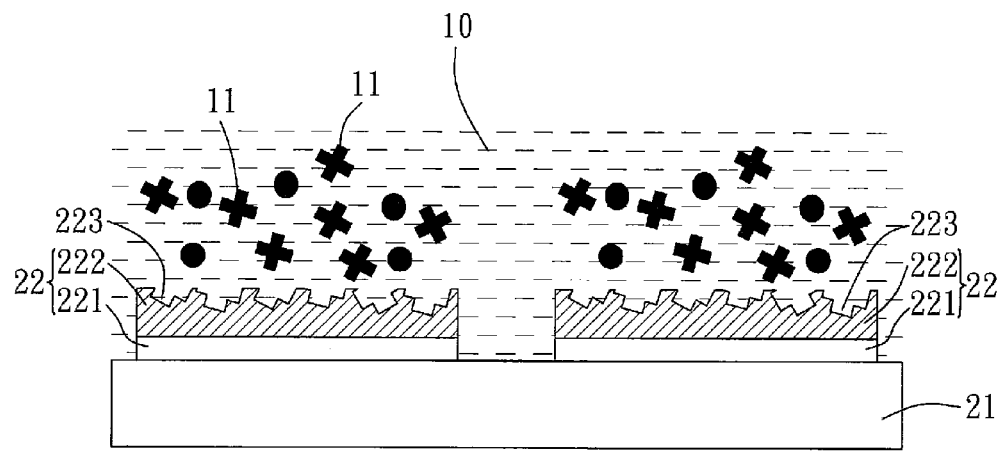
FIGS. 3A and 3B are schematic views illustrating an interaction between an analyte and the sensor electrodes.
Figure 3B:
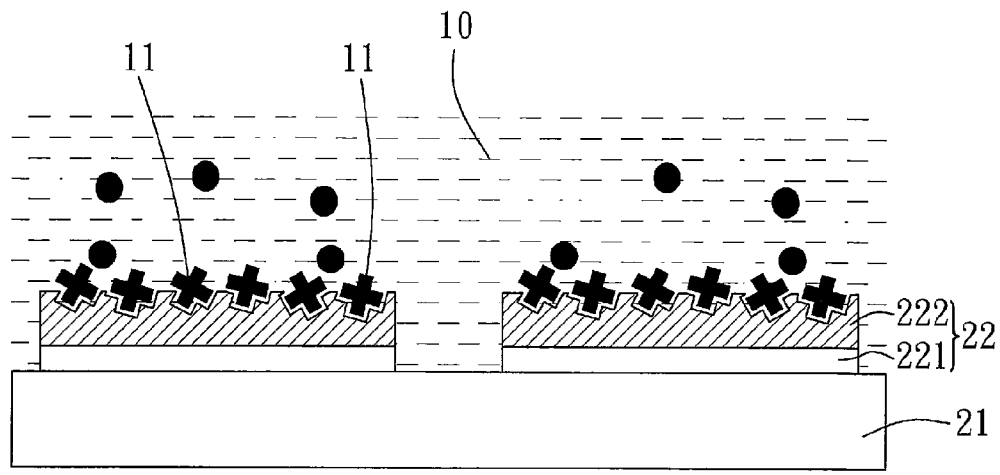

To carry out the method of the present invention, a solution 10 containing a known concentration of an analyte is introduced into the biosensor 2. Referring to FIGS. 3A and 3B, when the solution 10 is injected into the inner space 24 of the biosensor 2, the solution 10 is brought into contact with the sensor electrodes 22, and target molecules 11 of the analyte are captured by the molecular recognition cavities 223 of the molecularly imprinted conductive polymer film 222.

Figure 4:
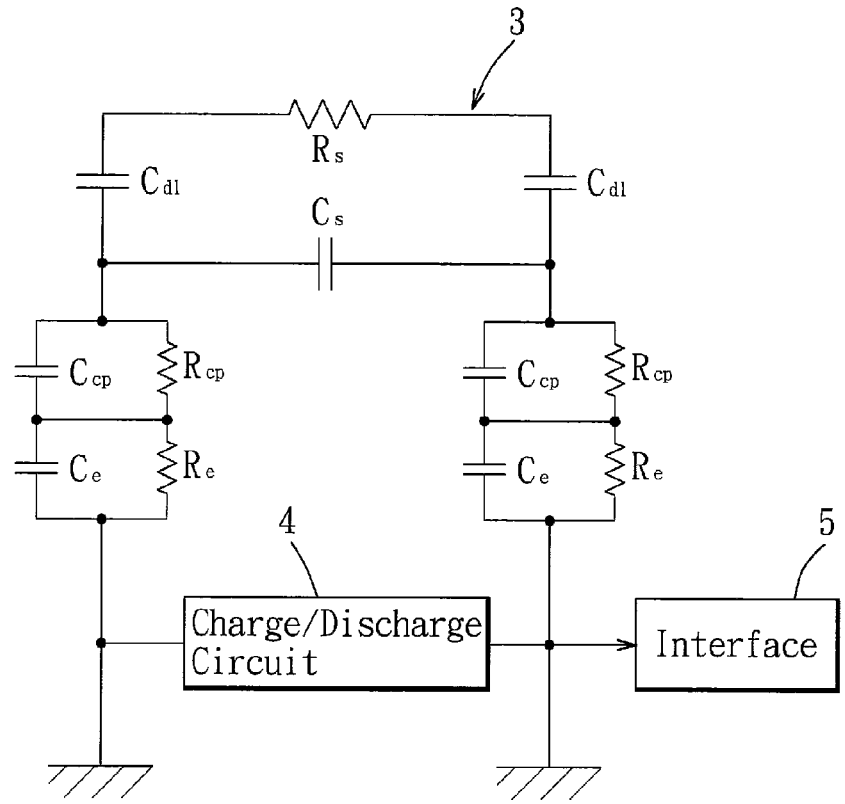
FIG. 4 is a schematic view illustrating an equivalent circuit of the biosensor connected to a charge/discharge circuit and an interface.

Referring to FIG. 4, the biosensor 2 has an equivalent circuit 3 and is connected to a charge/discharge circuit 4 that includes a discharge capacitor (not shown) coupled between the sensor electrode 22 of the biosensor 2. The equivalent circuit 3 includes metal film capacitance (electrode capacitance) (Ce), metal film resistance (electrode resistance) (Re), conductive polymer capacitance (Ccp), conductive polymer resistance (Rcp), solution capacitance (Cs), solution resistance (Rs), and double layer capacitance (Cdl).

The charge/discharge circuit 4 charges the biosensor 2 when a constant voltage is applied to the charge/discharge circuit 4. Preferably, the applied constant voltage is greater than 0.2V and less than 0.7V. When the applied voltage is less than 0.2V, inaccurate measurements of the voltage tends to occur. When the applied voltage is greater than 0.7V, the molecularly imprinted conductive polymer films 222 are likely to be burned down due to the effect of a high surge current during discharging.

After the charge/discharge circuit 4 and the biosensor 2 are saturatedly charged, the charge/discharge circuit 4 and the biosensor 2 are discharged. The charge/discharge circuit 4 is connected to an interface device 5. During the discharging of the charge/discharge circuit 4 and the biosensor 2, the interface device 5 is implemented to measure varying voltages across the discharge capacitor of the charge/discharge circuit 4 to obtain a set of voltage values that vary with time within the period of discharging. The varying voltage values exhibit the characteristics of the biosensor 2 associated with the concentration of the analyte detected by the biosensor. Preferably, the voltage values are measured during an initial period of discharge that elapses from the beginning of the discharging. When the discharging begins, electrons will recombine with charges in the solution 10 in a very short duration.

The voltage values measured during discharge has a characteristic parameter characterizing the biosensor 2, which is associated with the concentration of the analyte detected by the biosensor 2.

In order to obtain a set of reference data, which represent a relation between the characteristic parameter of the voltage values and the concentration of the analyte detected by the biosensor 2, a plurality of solution samples are prepared using different known concentrations of the analyte and are detected by the biosensor 2. A series of operations for charging and discharging the biosensor 2 are performed. During the operations, the biosensor is exposed to a set of solutions containing different known concentrations of the anesthetic for the respective operations. For each operation, the voltage values are measured during discharging, and the characteristics parameter of the voltage values is determined. The reference data may be obtained by developing a characteristic parameter-concentration relation based on the characteristics parameters of the voltage values obtained from the series of operations and the known concentrations detected by the biosensor 2.

Figure 5:
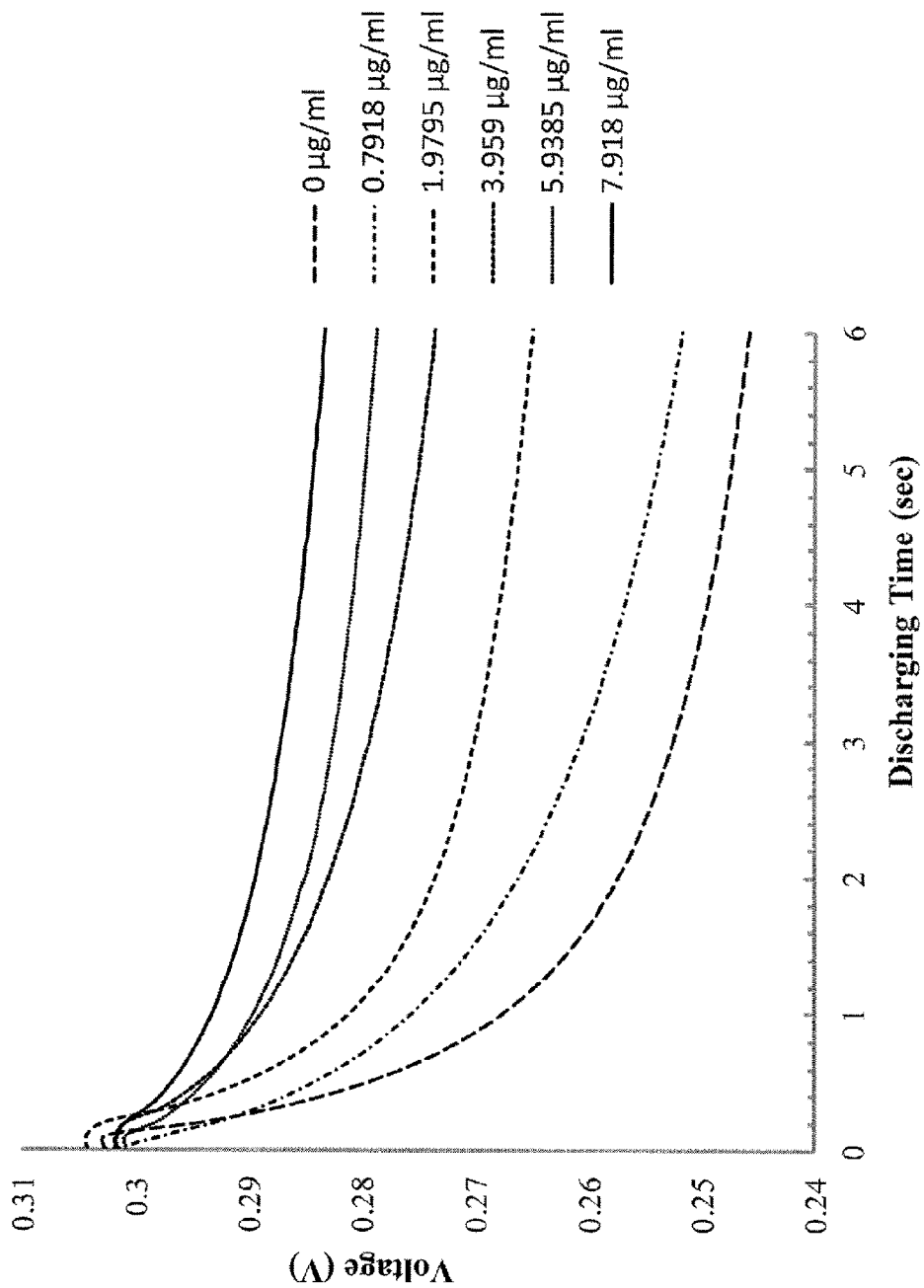
FIG. 5 is a diagram showing a set of voltage versus time curves obtained from the discharging of the biosensor at different concentrations of the analyte.

Referring to FIG. 5, a plurality of curves are shown representing multiple sets of the voltage values with respect to time, which are obtained for different known concentrations of the analyte detected by the biosensor 2. The characteristic parameters of the voltage values vary as the concentration of the analyte is varied.

Referring once again to FIG. 4, the interface 5 may be a USB DAQ device that can be implemented to process the varying voltage values measured during the discharging of the biosensor 2 and to determine the characteristic parameter of the voltage values. The characteristic parameter may be any parameter suitable to characterize the biosensor 2.

Figure 6:
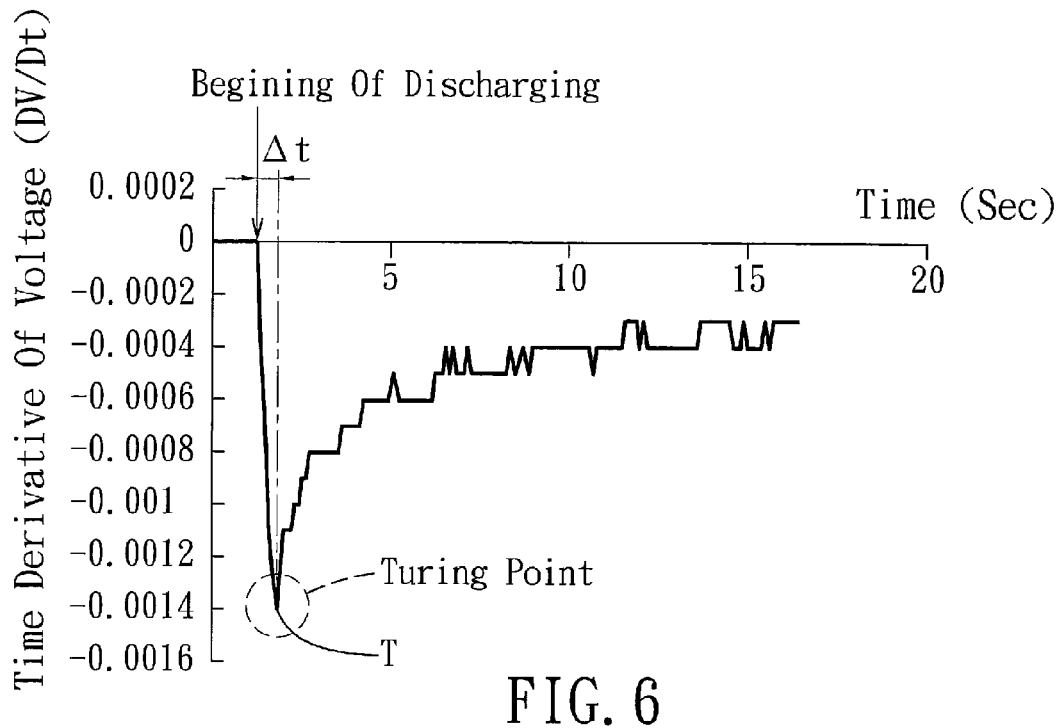
FIG. 6 is a diagram showing a plot of time derivative of voltage versus time having a turning point at which a second derivative of the voltage is zero.
Figure 7:
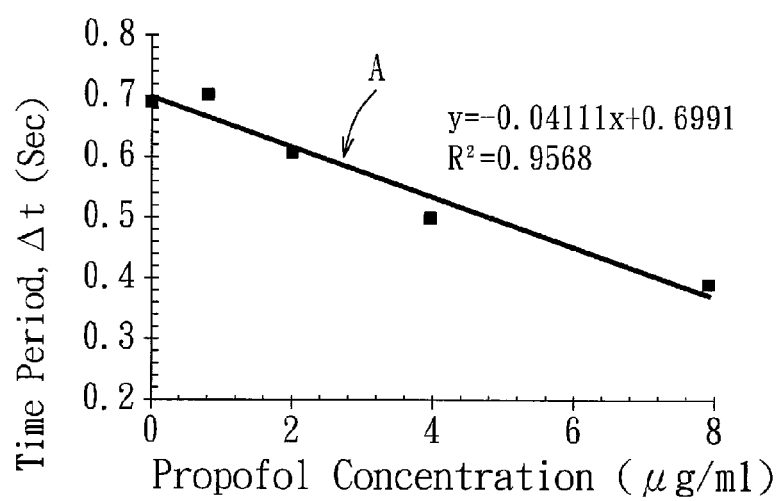
FIG. 7 is a diagram showing reference data in terms of a reference curve representing a relation between analyte concentration and a duration elapsed time from a beginning of discharge to the turning point.

In a preferred embodiment, the characteristic parameter is a duration time that elapses from the beginning of the discharging to a point where a second derivative of the voltage value is zero. The reference data used in this embodiment represent a relation between the duration time and the concentration of the analyte. Referring to FIG. 6, the second derivative of the voltage value is zero at a turning point (T) in curve (A), which is obtained by plotting the time derivatives (dv/dt) of the voltage values as a function of time. Referring to FIG. 7, the relation between the duration time and the concentration has good linearity as demonstrated by curve (A).

Figure 8:
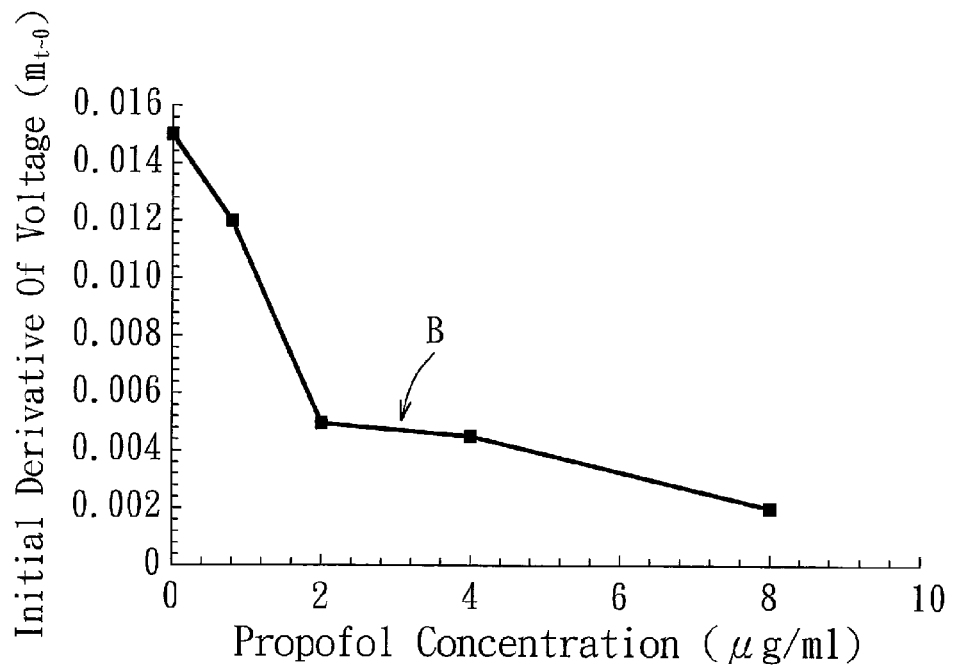
FIG. 8 is a diagram showing reference data in terms of a reference curve representing a relation between analyte concentration and the first derivative of an initial voltage value.

In another preferred embodiment, the characteristic parameter is the first derivative (dV/dt) of an initial voltage value obtained at the beginning of the discharging. The reference data used in this embodiment represent a relation between the first derivative (dV/dt) of the initial voltage value and the concentration. Referring once again to FIG. 5, the first derivative (dV/dt) of the initial voltage value obtained at the beginning of the discharging is shown in terms of a line of initial slope ($m_{t=0}$) (i.e., the time derivative of initial voltage $(dV/dt)_{t=0}$ at the analyte concentration of 0 μg/ml). Referring to FIG. 8, when the initial slope or the first derivative of initial voltage is plotted as a function of analyte concentration, a reference curve (B) may be obtained.

Figure 9:
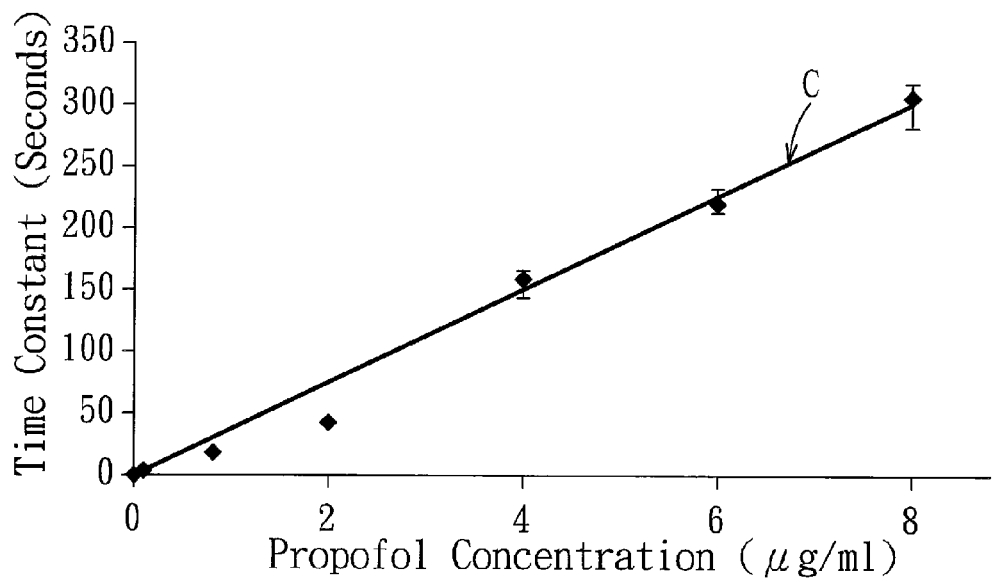
FIG. 9 is a diagram showing reference data in terms of a reference curve representing a relation between analyte concentration and the time constant of the voltage values.

In still another preferred embodiment, the characteristic parameter is a time constant parameter, and the reference data represent a relation between the time constant parameter and the concentration. The time constant parameter can be determined using the following equation:

$$V = V_0 e^{-t/RC} \tag{1}$$

where V represents the real time voltage value obtained by measurement during the discharging of the biosensor 2, $V_0$ represents the initial voltage value at the beginning of the discharging, t represents the elapsed time during the discharging, and RC is time constant. Referring to FIG. 9, the reference data in this embodiment may be shown in terms of a reference curve (C) (time constant versus concentration), which shows a linear relation between the time constant and the concentration of the analyte.

According to the present invention, an unknown concentration of the analyte can be determined by comparing the characteristic parameter (such as, the duration time, the first derivative of the initial voltage value, or the time constant obtained from the detection of the unknown concentration by the biosensor 2) with the reference data representing the relation between the characteristic parameter and concentration (see the reference curves (A), (B) and (C)).

The following Examples are provided to illustrate the merits of the preferred embodiments of the invention, and should not be construed as limiting the scope of the invention.

Example 1

A blank chip including a substrate and two gold layers (rectangular in shape and having a size of 2000 μm×200 μm) formed on the substrate and spaced apart from each other by a distance of 500 μm was prepared. Pyrrole monomer and propofol (serving as the template molecule) were mixed together, followed by mixing with methanol and KCl (serving as a doping ion) to form a solution having a pyrrole concentration of 9728 μg g/ml, a template molecule (propofol) concentration of 7131 μg/ml, and a doping ion concentration of 75 μg/ml. The blank chip was placed in the solution thus formed, followed by electropolymerizing by applying a positive voltage of 2V to the gold layers and grounding a platinum electrode for 60 seconds so as to form a conductive polymer film on each of the gold layers. The conductive polymer films thus formed on the gold layers were placed in a solvent of methanol to remove the template molecules therefrom, followed by drying so as to form an anesthetic biosensor.

A test solution containing 0.7918 μg/ml propofol (serving as the analyte) was prepared. An amount of the test solution was injected into the anesthetic biosensor. The anesthetic biosensor filled with the solution was charged by applying 0.3V to the anesthetic biosensor until a saturation voltage level was reached. Subsequently, the anesthetic biosensor was discharged. During the discharging of the anesthetic biosensor, the voltage change with respect to time was measured (see the curve labeled with 0.7918 μg/ml in FIG. 5). The time derivative of the voltage was calculated to determine which second derivative of the voltage is zero. A duration time from the beginning of discharging to the time of the turning point (where the second derivative of the voltage is zero) is about 0.71 second.

Examples 2-5

Examples 2-5 differ from Example 1 in that the analyte concentrations prepared for Examples 2-5 are 1.9795 μg/ml, 3.959 μg/ml, 7.918 μg/ml, and 0 μg/ml, respectively. The measured voltage changes with respect to time during discharging for Examples 2-5 are shown in FIG. 5. The duration times measured from the beginning of the discharging to the time of the turning point for Examples 2-5 are 0.62 second, 0.5 second, 0.39 second and 0.7 second, respectively.

The reference curve (A) in FIG. 7 is a duration time (Δt) versus concentration curve obtained from the experiments in Examples 1-5, and shows a linear relation. Hence, an unknown analyte concentration may be determined by measuring the duration time (Δt) for the unknown analyte concentration and by comparing the duration time with the reference data representing the relation between the concentration and the duration time, which is shown by the reference curve (A).

The reference curve (B) shown in FIG. 8 is also obtained from the experiments of Examples 1-5. The reference curve (B) also show a linear relation at a range between 0 μg/ml and 2 μg/ml and a range between 2 μg/ml and 8 μg/ml.

By charging and discharging the biosensor 2 and by using the molecularly imprinted conductive polymer films 222 in the sensor electrodes 22, an analyte concentration can be effectively and accurately determined.

While the present invention has been described in connection with what are considered the most practical and preferred embodiments, it is understood that this invention is not limited to the disclosed embodiments but is intended to cover various arrangements included within the spirit and scope of the broadest interpretation so as to encompass all such modifications and equivalent arrangements.

What is claimed is:

1. A method for determining a concentration of an anesthetic in a solution, comprising:
    (a) providing a biosensor that includes two sensor electrodes each of which has a metal layer and a molecularly imprinted polymer film formed on the metal layer, said molecularly imprinted polymer film being imprinted by a template molecule to form a plurality of molecular recognition cavities for capturing molecules of the anesthetic;
    (b) exposing the biosensor to the solution;
    (c) connecting a charge/discharge circuit to the biosensor that has been exposed to the solution, the charge/discharge circuit including a discharge capacitor coupled between the sensor electrodes;
    (d) applying a constant voltage to the charge/discharge circuit to charge the charge/discharge circuit and the biosensor;
    (e) discharging the charge/discharge circuit and the biosensor after the charge/discharge circuit and the biosensor are saturatedly charged;
    (f) measuring varying voltages across the discharge capacitor during discharge to obtain a set of varying voltage values that vary with time;
    (g) determining a characteristic parameter of the voltage values associated with the concentration of the anesthetic detected by the biosensor; and
    (h) determining the concentration of the anesthetic by comparing the characteristic parameter with reference data representing a relation between an anesthetic concentration and characteristic parameters of the biosensor.

2. The method of claim 1, wherein the reference data are obtained by: performing a series of operations for charging and discharging the biosensor while the biosensor is exposed to a set of solutions containing different known concentrations of the anesthetic for the respective operations; obtaining a set of voltage values during discharging of the biosensor after each of the operations; determining a characteristic parameter of the voltage values obtained for each of the operations; and developing the reference data based on the known concentrations and the characteristics parameters obtained for the operations.

3. The method of claim 1, wherein the characteristic parameter is a time parameter that elapses from the beginning of the discharging to a point where a second derivative of the voltage value is zero.

4. The method of claim 1, wherein the characteristic parameter is a first derivative of the voltage value obtained at the beginning of the discharging.

5. The method of claim 1, wherein the characteristic parameter is a time constant parameter.

6. The method of claim 1, wherein the constant voltage is greater than 0.2V and less than 0.7V.

7. The method of claim 1, wherein the voltage values are measured during an initial period of discharge that elapses from a beginning of the discharging of the biosensor.

8. The method of claim 1, wherein the molecularly imprinted polymer film is made from a conductive polymer formed from a monomer selected from pyrrole, acetylene, paraphenylene sulfide, thiophene, aniline, and isothionaphthene.

9. The method of claim 8, wherein the monomer is pyrrole.

10. The method of claim 1, wherein the anesthetic molecule is propofol.

11. The method of claim 1, wherein the metal layer is made from a noble metal.

12. The method of claim 11, wherein the metal layer is made from gold.

13. A method for determining a concentration of an analyte in a solution, comprising:
    (a) providing a biosensor that includes two sensor electrodes each of which has a metal layer and a molecularly imprinted polymer film formed on the metal layer;
    (b) exposing the biosensor to the solution;
    (c) connecting a charge/discharge circuit to the biosensor that has been exposed to the solution, the charge/discharge circuit including a discharge capacitor coupled between the sensor electrodes;
    (d) applying a constant voltage to the charge/discharge circuit to charge the charge/discharge circuit and the biosensor;
    (e) discharging the charge/discharge circuit and the biosensor after the charge/discharge circuit and the biosensor are saturatedly charged;
    (f) measuring varying voltages across the discharge capacitor during discharge to obtain a set of varying voltage values that vary with time;
    (g) determining a characteristic parameter of the voltage values that is associated with the concentration of the analyte detected by the biosensor; and
    (h) determining the concentration of the analyte by comparing the characteristic parameter with reference data representing a relation between an analyte concentration and the characteristic parameter of the biosensor.

14. The method of claim 13, wherein the characteristic parameter is a time parameter that elapses from the beginning of the discharging to a point where a second derivative of the voltage value is zero and where a plot of the first derivatives of the voltage value versus time exhibits a turning point.

15. The method of claim 13, wherein the characteristic parameter is a first derivative of the voltage value obtained at the beginning of the discharging.

16. The method of claim 13, wherein the characteristic parameter is a time constant parameter.

17. The method of claim 13, wherein the constant voltage is greater than 0.2V and less than 0.7V.

* * * * *